(12) United States Patent
Roeck et al.

(10) Patent No.: US 11,997,457 B2
(45) Date of Patent: *May 28, 2024

(54) HEARING DEVICE FOR PROVIDING PHYSIOLOGICAL INFORMATION, AND METHOD OF ITS OPERATION

(71) Applicant: SONOVA AG, Staefa (CH)

(72) Inventors: Hans-Ueli Roeck, Hombrechtikon (CH); Anne Thielen, Stäfa (CH)

(73) Assignee: Sonova AG, Staefa (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/960,960

(22) Filed: Oct. 6, 2022

(65) Prior Publication Data
US 2023/0036678 A1 Feb. 2, 2023

Related U.S. Application Data

(63) Continuation of application No. 17/185,649, filed on Feb. 25, 2021, now Pat. No. 11,516,598.

(30) Foreign Application Priority Data

Mar. 16, 2020 (EP) ..................................... 20163364

(51) Int. Cl.
*H04R 25/00* (2006.01)
(52) U.S. Cl.
CPC ......... *H04R 25/43* (2013.01); *H04R 2225/39* (2013.01); *H04R 2225/41* (2013.01); *H04R 2225/55* (2013.01)
(58) Field of Classification Search
CPC .. H04R 25/43; H04R 1/1041; H04R 2225/39; H04R 2225/41; H04R 2225/55; A61B 5/165

USPC ........ 381/312, 74, 58, 67, 56; 600/586, 528, 600/301, 25, 27, 28, 559
See application file for complete search history.

(56) References Cited

U.S. PATENT DOCUMENTS

| | | | |
|---|---|---|---|
| 9,579,060 B1 | 2/2017 | Lisy et al. | |
| 2008/0287752 A1* | 11/2008 | Stroetz | A61B 5/6817 600/301 |
| 2013/0060168 A1* | 3/2013 | Chu | A61B 5/6803 600/595 |

(Continued)

FOREIGN PATENT DOCUMENTS

EP 3525490 8/2019

OTHER PUBLICATIONS

"Extended European Search Report received in EP Application No. 20163364.1 on Mar. 16, 2020."

*Primary Examiner* — Norman Yu
(74) *Attorney, Agent, or Firm* — ALG Intellectual Property, LLC

(57) ABSTRACT

A hearing device configured to be worn at an ear of a user may include a sensor unit configured to provide sensor data, the sensor unit comprising a sound detector configured to provide sound data included in the sensor data; and a processor configured to determine a physiological parameter from the sensor data, the physiological parameter indicative of a physiological property of the user. The processor is configured to determine whether the physiological parameter fulfills a condition, and provide, depending on whether the physiological parameter fulfills the condition, output data based on the sensor data.

18 Claims, 5 Drawing Sheets

(56) References Cited

U.S. PATENT DOCUMENTS

| | | |
|---|---|---|
| 2017/0112671 A1 | 4/2017 | Goldstein |
| 2017/0215011 A1* | 7/2017 | Goldstein ............ H04R 25/305 |
| 2017/0251933 A1 | 9/2017 | Braun et al. |
| 2018/0368718 A1* | 12/2018 | Koziol ................. A61B 5/6815 |
| 2019/0082974 A1 | 3/2019 | Leboeuf et al. |

* cited by examiner

HEARING DEVICE FOR PROVIDING PHYSIOLOGICAL INFORMATION, AND METHOD OF ITS OPERATION

RELATED APPLICATIONS

The present application is a continuation application of U.S. patent application Ser. No. 17/185,649, filed Feb. 25, 2021, which claims priority to EP Patent Application No. 20163364.1, filed Mar. 16, 2020, the contents of which are hereby incorporated by reference in their entirety.

BACKGROUND INFORMATION

Hearing devices are typically used to improve the hearing capability or communication capability of a user, for instance by compensating a hearing loss of a hearing-impaired user, in which case the hearing device is commonly referred to as a hearing instrument such as a hearing aid, or hearing prosthesis. The hearing device may pick up the surrounding sound with a microphone, process the microphone signal thereby taking into account the hearing preferences of the user of the hearing device, and provide the processed sound signal to an output transducer stimulating the user's hearing. The output transducer can be a miniature loudspeaker, commonly referred to as a receiver, for producing a sound in the user's ear canal. As another example, the output transducer can be an electrode array of a cochlear implant producing electric signals stimulating the auditory nerve. A hearing device may also be used to produce a sound in a user's ear canal based on an audio signal which may be communicated by a wire or wirelessly to the hearing device. Hearing devices are often employed in conjunction with communication devices, such as smartphones, for instance when listening to sound data processed by the communication device and/or during a phone conversation operated by the communication device. More recently, communication devices have been integrated with hearing devices such that the hearing devices at least partially comprise the functionality of those communication devices.

Some hearing devices have been equipped with a biometric sensor. The biometric sensor is usually employed to collect biological information from the user allowing to monitor the user's health. Biometric data provided by the sensor may include, for instance, a photoplethysmography (PPG) signal, an electroencephalography (EEG) signal, an electrocardiography (ECG) signal, an electrooculography (EOG) signal, a temperature measurement signal, a skin conductance signal, and/or the like. Including the biometric sensor in a hearing device can offer the advantage of placing the sensor at a rather central body position at the ear such as, for instance, inside the ear canal. Such a sensor placement can contribute to an increased accuracy and/or reliability of the biometric data for a variety of reasons including a good blood circulation, a rather stable sensor position, decreased external light exposure, a proximity to the user's brain, and can also be favourable in preserving the user's mobility as compared to sensor placements at other body positions.

Including a biometric sensor in a hearing device, however, also poses technical challenges which are mainly caused by inherent size restrictions and a limited energy supply. Obtaining meaningful physiological parameters from the biometric data often requires an expensive processing and/or storage space of the biometric data which may reach practical limits set by the processing and memory capabilities offered by current hearing devices. Yet some physiological parameters can be extracted more easily than others. For instance, determining a pulse rate from a PPG waveform can be less cumbersome than obtaining a blood pressure value. Determining a change of neural activity in an EEG recording can require less processing and memory consumption than extracting a certain type of neural oscillations from the biometric data, for instance to identify a certain type of cognitive process. In order to accomplish the more complex task, the biometric data can be transmitted from the hearing device to a remote device with higher processing power and larger memory such as a smartphone or a personal computer. Continuous data exchange and/or transmission of big data volumes, however, can raise other problems associated with an increased energy consumption required for the data transfer and a limited energy supply that can be provided by a hearing device due to size restrictions for the incorporation of a battery.

Furthermore, the meaningfulness of some physiological parameters depends on certain conditions met by other physiological parameters. For instance, a blood pressure value may only be useful as a medical indicator when the pulse rate of the user corresponds to his resting heart rate (RHR). The individual RHR, in turn, is preferentially determined in a physiological meaningful way when other physiological conditions of the user are met. Current methods of determining the individual RHR therefore require the user to remain in a resting position for a certain time in which his body activities including physical movements, emotional distress, and mental efforts are reduced to a minimum. Determining the RHR ad hoc in such a manner can be rather impractical in some life situations, whereas in other life situations the required physiological conditions may be met by the user without any intention to learn about his RHR.

U.S. patent application publication No. US 2019/0082974 A1 discloses a hearing device equipped with a biometric sensor including an optical emitter and an optical detector to provide PPG data from the user's ear. The hearing device further includes an inertial sensor configured to measure a physical motion of the ear which can be employed as a noise reference for an adaptive filter to remove motion artifacts from the PPG data. Physiological parameters of interest can then be determined from the PPG data including a heart rate, a blood flow, a heart rate variability, a respiration rate, a blood gas/analyte level, a maximum oxygen consumption ($VO_2$ max), and a blood pressure. Continuously determining those parameters over time, however, can be rather processing intensive depending on the complexity of a physiological assessment algorithm applied to obtain the respective parameter. Such an algorithm may also be executed by a device remote from the hearing device causing, however, high energy consumption required for the data transmission.

BRIEF DESCRIPTION OF THE DRAWINGS

Reference will now be made in detail to embodiments, examples of which are illustrated in the accompanying drawings. The drawings illustrate various embodiments and are a part of the specification. The illustrated embodiments are merely examples and do not limit the scope of the disclosure. Throughout the drawings, identical or similar reference numbers designate identical or similar elements. In the drawings.

DETAILED DESCRIPTION

Figure 1:
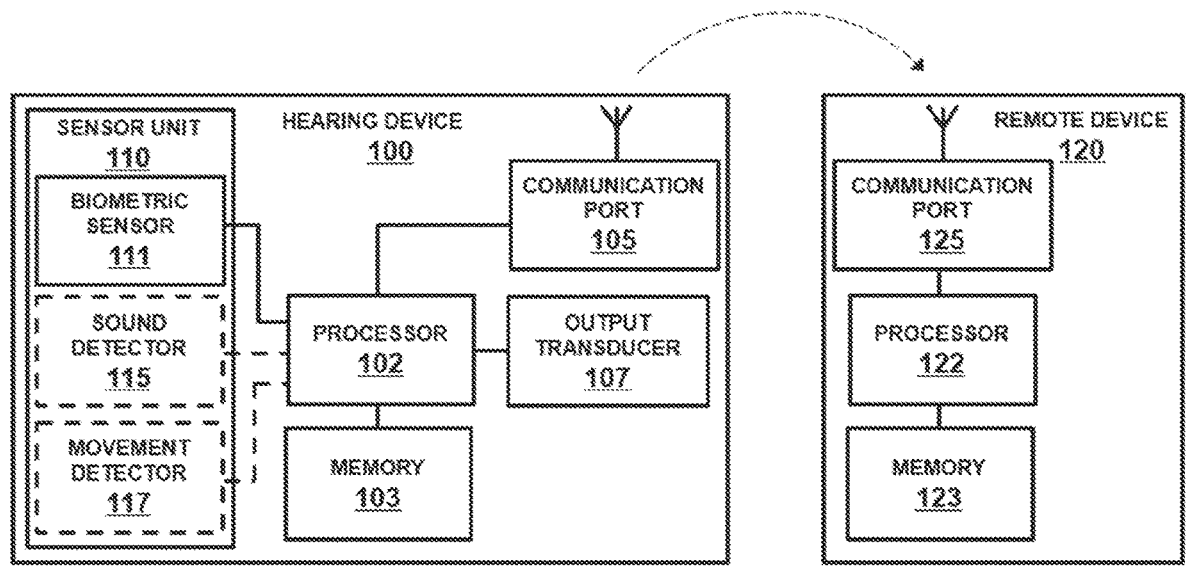
FIG. 1 schematically illustrates an exemplary hearing device including a processor, a sensor unit including a biometric sensor, and an output transducer, and an exemplary remote device communicatively coupled to the hearing device.

The disclosure relates to a hearing device configured to be worn at an ear of a user, the hearing device comprising a sensor unit configured to provide sensor data, the sensor unit comprising a biometric sensor configured to provide biometric data included in the sensor data, and a processor configured to determine a physiological parameter from the sensor data, the physiological parameter indicative of a physiological property of the user. The disclosure also relates to a method of operating a hearing system, and a computer-readable medium storing instructions for performing the method. The disclosure also relates to a communication system comprising the hearing device and a remote device, a method of operating a communication system, and a computer-readable medium storing instructions for performing the method.

It is a feature of the present disclosure to avoid at least one of the above mentioned disadvantages and to provide a hearing device and/or a method of operating the hearing device in which the biometric data produced by the biometric sensor can be evaluated in a more efficient way, in particular such that an amount of required data processing and/or memory usage and/or energy consumption of the hearing device can be effectively reduced. It is another feature to allow determining of a physiological parameter in a more reliable way, for instance in a context of mutually related parameters in which a physiological parameter depends on a condition met by at least one other physiological parameter. It is a further feature to output biometric data and/or information derived from the biometric data characteristic for a physiological condition of the user.

Accordingly, the present disclosure proposes a hearing device configured to be worn at an ear of a user, the hearing device comprising a sensor unit configured to provide sensor data, and a processor configured to determine a physiological parameter from the sensor data, the physiological parameter indicative of a physiological property of the user; to determine whether the physiological parameter fulfills a condition; and to provide, depending on whether the physiological parameter fulfills the condition, output data based on the sensor data, the output data including at least part of the biometric data and/or information derived from at least part of the biometric data different from said physiological parameter.

The output data may thus be provided with biometric data and/or information derived from the biometric data which is relevant for a situation in which the physiological parameter determined from the sensor data fulfills the condition. The biometric data and/or information derived from the biometric data included in the output data may thus be effectively reduced to data relevant for a specific physiological condition. Additionally or alternatively, a number of times at which the output data is provided may be effectively reduced to the times at which the physiological parameter fulfills the condition. The output data can thus be provided with increased efficiency allowing a more efficient data evaluation. The reliability of a physiological parameter included in the information in the output data different from said physiological parameter fulfilling the condition or a physiological parameter derived from the output data can also be enhanced. For instance, when such a physiological parameter included in or derived from the output data depends on at least one different physiological parameter which is determined to fulfill the condition, it can be ensured that the output data accounts for the dependency between the physiological parameter included in or derived from the output data and the different physiological parameter by the determining that the different physiological parameter fulfills the condition. In particular, the output data may be provided such that it is characteristic for a physiological condition of the user, which may be indicated by the physiological parameter fulfilling the condition.

Independently, the present disclosure proposes a method of operating a hearing device configured to be worn at an ear of a user. The method comprises providing sensor data including biometric data detected from the user; determining a physiological parameter from the sensor data, the physiological parameter indicative of a physiological property of the user; determining whether the physiological parameter fulfills a condition; and providing, depending on whether the physiological parameter fulfills the condition, output data based on the sensor data, the output data including at least part of the biometric data and/or information derived from at least part of the biometric data different from said physiological parameter. Independently, the present disclosure proposes a non-transitory computer-readable medium storing instructions that, when executed by a processor, cause a hearing device to perform operations of the method.

The present disclosure also proposes a communication system comprising the hearing device and a remote device comprising a communication port configured to receive the output data transmitted from a communication port of the hearing device. The present disclosure further proposes a method of operating a communication system comprising a hearing device and a remote device, the method comprising transmitting the output data to the remote device; and determining, by the remote device, a physiological parameter from the output data. Independently, the present disclosure proposes a non-transitory computer-readable medium storing instructions that, when executed by a processor of the hearing device and/or remote device, cause a communication system to perform operations of the method.

Subsequently, additional features of some implementations of the hearing device and/or the communication system and/or the method of operating a hearing device and/or a communication system are described. Each of those features can be provided solely or in combination with at least another feature. The features can be correspondingly provided in some implementations of the hearing device and/or the communication system and/or the method of operating the hearing device and/or the method of operating the communication system and/or the computer-readable medium.

In some implementations, the hearing device comprises a communication port configured to transmit data to a remote device, wherein the processor is configured to provide the output data to the communication port. The communication port of the hearing device may be configured for wireless data transmission to a communication port of the remote device. The remote device can comprise a processor configured to determine a physiological parameter from the output data transmitted from the hearing device in a subsequent processing. The subsequent processing of the output data may be employed to determine the physiological parameter from the output data in a more complex and/or expensive processing algorithm as compared to the processing required for determining the physiological parameter for which the condition is determined to be fulfilled by the hearing device. The physiological parameter determined by the remote device may be a second physiological parameter different from a first physiological parameter determined by the processor of the hearing device, based on which first physiological parameter the condition is determined to be fulfilled by the processor of the hearing device. The remote device may be configured to determine the second physiological parameter with an enhanced processing performance and/or an increased memory investment as compared to a processing performance and/or a memory that would be available in the hearing device. An energy consumption or memory investment of the hearing device required for determining the second physiological parameter from the output data may thus be reduced. The remote device may be a device configured to be operated remote from the user's ear. For instance, the remote device may be a handheld device, such as a smartphone, or a stationary device, such as a personal computer.

The output data may be transmitted to the remote device depending on whether the condition of the physiological parameter determined by the hearing device is fulfilled. An energy consumption of the hearing device required for the transmission of the output data can thus also be reduced. The processor of the remote device can then determine the different physiological parameter from the output data depending on whether the condition of the physiological parameter determined by the hearing device is fulfilled. For instance, the output data may only be transmitted to the remote device when it is relevant for the determining of the different physiological parameter from the output data by the remote device, which can depend on the condition being fulfilled by the physiological parameter determined by the hearing device.

In some instances, the processor of the hearing device is configured to provide the output data including at least part of the biometric data. In some instances, the processor is configured to provide the output data including information derived from at least part of the biometric data different from said physiological parameter. In some instances, the processor is configured to provide the output data including at least part of the biometric data and information derived from at least part of the biometric data different from said physiological parameter. The output data may be provided, when the physiological parameter fulfills the condition. The output data may not be provided, when the physiological parameter does not fulfill the condition.

In some implementations, the physiological parameter is a first physiological parameter indicative of a first physiological property of the user. The processor of the hearing device may be configured to provide, depending on whether the first physiological parameter fulfills the condition, output data based on the sensor data, the output data including at least part of the biometric data and/or information derived from at least part of the biometric data different from said first physiological parameter, wherein the processor of the hearing device and/or a processor of a remote device is configured to subsequently process the output data in order to determine a second physiological parameter indicative of a second physiological property of the user, the second physiological parameter different from the first physiological parameter and the second physiological property different from the first physiological property.

In some implementations, biometric information in the biometric data included in the output data is unmodified by the processor. The output data may thus comprise at least part of the biometric data including the biometric information as provided by the biometric sensor unmodified by the processor of the hearing device. The term "unmodified" may imply that the biometric data included in the output data contains the same amount of information relevant for a biometric property measured by the biometric sensor as the biometric data provided by the biometric sensor. In some instances, the output data comprises at least part of the biometric data processed by the processor, for instance to reduce noise and/or to remove artifacts such as movement artifacts, wherein the biometric data in the output data contains the same amount of information relevant for the biometric property as the biometric data provided by the biometric sensor.

In some instances, the output data includes at least part of the biometric data unprocessed by the processor. The biometric data included in the output data may thus be accessible in an original and/or raw form in which it has been provided by the biometric sensor, in particular in a form in which it has been included in an output signal of the biometric sensor. A subsequent processing of the biometric data included in the output data can then be based on the unprocessed biometric data. A more complex and/or expensive subsequent processing algorithm may then be performed in a superior way, in particular based on uncompromised information included in the biometric data, which may provide a gain in information and/or a higher reliability of the physiological parameter determined from the output data. A number of times of performing the more complex and/or expensive processing algorithm can thus be advantageously reduced to events for which the condition is determined to be fulfilled by the hearing device. The subsequent processing may be performed by the processor of the remote device and/or by the processor of the hearing device. Thus, the energy consumption required by the hearing device for performing the more complex and/or expensive processing algorithm and/or for transmitting the output data such that the more complex and/or expensive processing algorithm can be performed by the remote device can be reduced.

In some implementations, the output data comprises information derived from at least part of the biometric data. The derived information may include the physiological parameter for which it is determined whether the condition is fulfilled. The derived information may include another physiological parameter determined from the sensor data.

In some implementations, the processor is configured to repeatedly determine the physiological parameter over a period, wherein the output data is provided when the physiological parameter fulfills the condition within the period. The condition may thus be determined to be fulfilled at a higher reliability. In some instances, the condition includes the additional requirement to be fulfilled for a plurality number of times within the period, in particular over the whole period. This may imply determining whether the condition is fulfilled for a predetermined number of times, in particular each time, at which the physiological parameter has been determined within the period.

In some implementations, the determining whether the physiological parameter fulfills the condition comprises determining evaluating the physiological parameter relative to a threshold. This may comprise determining whether the physiological parameter falls below or rises above the threshold.

In some implementations, the physiological parameter is a first physiological parameter and the condition is a first condition, wherein the processor is configured to determine a second physiological parameter from the sensor data and to determine whether the second physiological parameter fulfills a second condition. The first physiological parameter and the second physiological parameter may be indicative for the same physiological property of the user. For instance, the physiological property may be a relaxation level of the user. The first physiological parameter and the second physiological parameter may also be indicative for a different physiological property of the user. For instance, a first physiological property indicated by the first physiological parameter may include a relaxation level, and a second physiological property indicated by the second physiological parameter may include a heart rate. As another example, the first physiological property may include a concentration level of the user and the second physiological property may include a body temperature.

In some instances, the output data is provided when the physiological parameter fulfills at least one of the first condition and the second condition. In some instances, the output data is provided when the physiological parameter fulfills both the first condition and the second condition. In some instances, the determining whether the first physiological parameter fulfills the first condition may comprise evaluating the first physiological parameter relative to a first threshold, and the determining whether the second physiological parameter fulfills the second condition may comprise evaluating the second physiological parameter relative to a second threshold. In some instances, the processor of the hearing device and/or a processor of a remote device is configured to subsequently process the output data in order to determine a third physiological parameter, the third physiological parameter different from the first physiological parameter and the second physiological parameter.

In some implementations, the physiological parameter is indicative of a heart rate of the user, wherein the determining whether the condition is fulfilled comprises determining whether the heart rate corresponds to a resting heart rate of the user. The output data may then be representative for a physiological state of the user at his resting heart rate. A physiological parameter determined from the output data may comprise another blood parameter depending on the resting heart rate, for instance a blood pressure at the resting heart rate. Another physiological parameter determined from the output data may comprise a body temperature of the user and/or a sweat rate of the user and/or a respiratory rate of the user and/or a cognitive parameter, for instance a cognitive load and/or a physiological stress and/or a listening intention of the user, at the resting heart rate.

In some implementations, the physiological parameter is indicative of a relaxation level of the user, wherein the determining whether the condition is fulfilled comprises determining whether the physiological parameter rises above a threshold. The output data may then be representative for a physiological state of the user at a high relaxation level. The physiological parameter may be a first physiological parameter. A physiological parameter determined from the output data, which may be denoted as a second physiological parameter, may comprise a blood parameter depending on the high relaxation level, for instance a resting heart rate and/or a blood pressure at the resting heart rate and/or a saturation pressure level of blood oxygen ($SpO_2$ level) at the resting hart rate. Another physiological parameter determined from the output data may comprise a body temperature of the user and/or a sweat rate of the user and/or a respiratory rate of the user and/or a cognitive parameter at the high relaxation level.

In some implementations, the physiological parameter is indicative of a heart rate and/or a resting heart rate and/or a heart rate variability (HRV) and/or a heart rate recovery time and/or a blood pressure and/or hypertension and/or a maximum oxygen consumption ($VO_2$ max) and/or a blood glucose level and/or a cardiovascular health level and/or an endurance level and/or an aerobic fitness level and/or a body temperature and/or a sweat rate and/or a respiratory rate and/or a cognitive load and/or a listening intention and/or a listening effort and/or a cognitive decline and/or a breakdown of neural activity over time and/or a sleeping or waking state and/or a distraction level and/or a concentration level and/or a relaxation level and/or a physical exhaustion level and/or a physiological stress level. Determining whether the condition is fulfilled may comprise determining whether the physiological parameter falls below or rises above a threshold. Determining whether the physiological parameter falls below or rises above the threshold may include a statistical evaluation, for instance an averaged value and/or a certain percentile of the physiological parameter falling below or rising above the threshold.

In some implementations, the physiological parameter can be indicative of a quality of physiological information represented by the biometric data, for instance a quality defined by the condition determined to be fulfilled. The condition may be representative for a physiological state of the physiological property. The physiological state may comprise a high relaxation level of the user, a heart rate corresponding to the resting heart rate, a presence of hypertension, a sleeping state of the user, a high cognitive load of the user, a high concentration level of the user, a large respiration rate, and/or the like.

In some implementations, the physiological parameter is at least partially determined from the biometric data. In some instances, the biometric data comprises PPG data and/or ECG data and/or EEG data and/or EOG data and/or temperature data and/or skin conductance data. The biometric sensor may comprise a PPG sensor and/or an ECG sensor and/or an EEG sensor and/or an EOG sensor and/or a temperature sensor and/or a skin conductance sensor and/or a radio frequency (RF) sensor.

In some implementations, the sensor unit comprises a movement detector configured to provide movement data included in the sensor data, wherein the physiological parameter is at least partially determined from the movement data. The movement detector may comprise an inertial sensor, in particular an accelerometer and/or a gyroscope and/or a magnetometer and/or a compass and/or a barometer and/or a navigation sensor (e.g. a GPS sensor). A physiological parameter determined from the movement data may comprise an amount and/or type of movements performed by the user. Determining whether the condition is fulfilled may comprise determining whether the amount and/or type of movements falls below or rises above a movement threshold. Different types of movement may include walking and/or running and/or cycling and/or climbing and/or shaking.

In some implementations, the sensor unit comprises a sound detector configured to provide sound data included in the sensor data, wherein the physiological parameter is at least partially determined from the sound data. In some instances, the sound detector is configured to detect sound in an environment of the user. In some instances, the sound detector is configured to detect sound from an own voice activity of the user. The sound detector may comprise a microphone, in particular a microphone array, and/or a voice activity detector (VAD) and/or a speaker recognition detector and/or a speech type detector and/or a body sound detector. The body sound detector may be sensitive for body sounds, which may include at least one of gulping, eating, burping, and digestion sounds. In some instances, the physiological parameter comprises a sound level, wherein the determining whether the condition is fulfilled comprises determining whether the sound level falls below or rises above a threshold. For instance, the sound level may be an own speech level and/or a body sound level, wherein the determining whether the condition is fulfilled comprises determining whether the own speech level and/or body sound level falls below or rises above a threshold, at least within an statistical evaluation relative to the threshold.

In some instances, the hearing device comprises a sound classifier configured to classify the sound data in different sound classes by assigning the sound data to a class from a plurality of classes. Each class assigned to the sound data may correspond to a state of the sound classifier. The classifier may determine a characteristic from the sound data and classify the sound data depending on the determined characteristic. The classes may comprise at least two classes associated with different audio processing parameters which can be applied by the processor of the hearing device for a processing of the sound data before the processed sound data is output by an output transducer of the hearing device to stimulate the user's hearing. The classes may represent a specific content in the sound data. Exemplary classes include, but are not limited to, low ambient noise, high ambient noise, traffic noise, music, machine noise, babble noise, public area noise, background noise, speech, non-speech, speech in quiet, speech in babble, speech in noise, speech from the user, speech from a significant other, background speech, speech from multiple sources, and/or the like.

The physiological parameter may comprise a selected class of the plurality of classes to which the sound data can be assigned, wherein the determining whether the condition is fulfilled comprises determining whether a current class assigned to the sound data corresponds to the selected class. The physiological parameter may comprise a selected state of the sound classifier corresponding to the selected class, wherein the determining whether the condition is fulfilled comprises determining whether a current state of the sound classifier corresponds to the selected state. For instance, a selected class assigned to the sound data may be representative for a low sound level in the ambient environment and/or no speech from the user which may be indicative of a high relaxation level of the user. A selected state of the sound classifier may be a state corresponding to the selected class. Determining whether the current class assigned to the sound data corresponds to the selected class may include a statistical evaluation of the class assigned to the sound data relative to the selected class.

In some implementations, the physiological parameter indicative of a relaxation level of the user is determined based on the physiological parameter indicative of a heart rate and/or the physiological parameter indicative of a heart rate variability (HRV). For instance, a higher relaxation level may be determined when the heart rate is determined to be closer to the resting heart rate (RHR), and a lower relaxation level may be determined when the heart rate is determined to be further off the RHR. As another example, a higher relaxation level may be determined when the HRV is determined to have a larger value, and a lower relaxation level may be determined when the HRV is determined to have a smaller value. To this end, the heart rate and/or HRV may be evaluated relative to a threshold value. For example, the threshold value of the heart rate may be provided as a certain percentage of the RHR added to the RHR, e.g. 10 percent of the RHR added to the RHR. As another example, the threshold value may be provided as a predetermined limit of the HRV, e.g., to provide a specific example, a value of 40 milliseconds. The relaxation level may then be determined as high when the heart rate is determined to be equal or smaller than the threshold value and/or when the HRV is determined to be equal or larger than the threshold value. The relaxation level may be determined as low, when the heart rate is determined to be larger than the threshold value and/or when the HRV is determined to be smaller than the threshold value.

In some implementations, the physiological parameter determined from the movement data and/or from the sound data is indicative of a relaxation level of the user. The physiological parameter determined from the movement data may comprise information about a physical activity of the user, wherein a smaller value of the physical activity indicates a higher relaxation level of the user. To illustrate, when no physical activity of the user has been determined for a certain time span, e.g. several minutes, an indication of a high relaxation level of the user may be deduced. The physiological parameter determined from the sound data may comprise a sound level, wherein a smaller value of the sound level indicates a higher relaxation level of the user. To illustrate, the lower the sound level the more probable is a high relaxation level of the user. The physiological parameter determined from the sound data may comprise a state of the sound classifier. The state can be indicative of a quality of a sound scene in the ambient environment. For instance, the state may comprise a quiet state at a rather silent environment and a speech state when speech is detected in the environment and/or from the user, and the like. The state of the sound classifier can thus also be indicative for the relaxation level of the user. For instance, the quiet state of the sound classifier may indicate a high relaxation level. The physiological parameter determined from the movement data may comprise a level and/or duration of movements carried out by the user indicative of the relaxation level of the user and/or a body position of the user indicative of the relaxation level of the user and/or an indicator of the hearing device being worn by the user. To illustrate, little and short movements carried out by the user and/or a reclined body position of the user can indicate a high relaxation level of the user, in particular when it is also determined that the hearing device is worn by the user.

In some implementations, the physiological parameter determined from the sound data is indicative of a distraction level of the user. The physiological parameter may comprise a sound level and/or a state of the sound classifier. To illustrate, the higher the sound level and/or a state of the sound classifier at a rather noisy environment can indicate a high distraction level of the user. In some implementations, the physiological parameter determined from the movement data is indicative of a physical exhaustion level of the user. The physiological parameter may comprise a level and/or duration of movements carried out by the user and/or a body position of the user. To illustrate, many movements carried out by the user and/or a walking activity of the user over a longer duration can indicate a high physical exhaustion level. The physiological parameter may indicate a trend and/or a rate of change of the physiological property underlying the physiological parameter.

In some implementations, the physiological parameter indicative of a relaxation level of the user is determined from the movement data and/or from the sound data, and the condition is determined to be fulfilled when the physical parameter indicates a high relaxation level. The output data may then be associated with a resting heart rate of the user. To illustrate, when the condition is determined to be fulfilled, it can be concluded that a momentary heart rate of the user can be associated with the resting heart rate of the user. The biometric data included in the output data can thus also be associated with the resting heart rate of the user. The output data may thus be employed, for instance, to determine a blood pressure of the user at the resting heart rate.

In some implementations, the physiological parameter is determined from a combination of multiple biometric sensor data, e.g. PPG data and/or ECG data and/or EEG data and/or EOG data and/or temperature data and/or skin conductance data, and/or a combination of biometric sensor data and movement data and/or a combination of biometric sensor data and sound data and/or a combination of biometric sensor data and movement data and sound data. In some implementations, the physiological parameter determined from the sensor data is indicative of a medical condition, for instance fever and/or sickness. In some implementations, the physiological parameter determined from the sensor data is indicative of uncontrolled movements of the user, such as shaking and/or jerking. The physiological parameter may be determined, for instance, from movement data and/or biometric data.

The physiological parameter determined by the hearing device may be a first physiological parameter. For instance, the first physiological parameter may be indicative of a heart rate of the user and/or indicative of a relaxation level of the user. Depending on whether the first physiological parameter fulfills the condition, the output data may be transmitted from the hearing device to a remote device determining a second physiological parameter from the output data, for instance a blood pressure.

In some implementations, the biometric sensor comprises a light source configured to emit light through a skin of the user and an optical detector for detecting a reflected and/or scattered part of the light, wherein the biometric data comprises information about the detected light. In particular, the biometric data may comprise information about blood volume changes indicated in an photoplethysmography (PPG) measurement. In some implementations, the biometric sensor comprises an electrode configured to detect an electric signal induced through a skin of the user, wherein the biometric data comprises information about the electric signal. In particular, the biometric data may comprise information about a brain activity indicated in an electroencephalogram (EEG) measurement and/or information about a heart activity indicated in an electrocardiogram (ECG) measurement and/or information about an eye activity indicated in an electrooculography (EOG) measurement. In some implementations, the biometric sensor comprises a temperature sensor configured to detect a body temperature of the user, wherein the biometric data comprises information about the body temperature. In some implementations, the biometric sensor comprises a radio frequency (RF) sensor configured to send energy at a radio frequency into tissue of the user and to detect a reflection and/or absorption thereof, for instance to determine an amount and/or density of certain molecules.

FIG. 1 illustrates an exemplary hearing device 100 configured to be worn at an ear of a user. Hearing device 100 may be implemented by any type of hearing device configured to enable or enhance hearing by a user wearing hearing device 100. For example, hearing device 100 may be implemented as a hearing instrument such as a hearing aid configured to detect sound and to provide an amplified version of the detected sound to a user, a cochlear implant system configured to provide electrical stimulation representative of the detected sound to a user, a bimodal hearing system configured to provide both amplification and electrical stimulation representative of the detected sound to a user, or any other suitable hearing prosthesis. In other examples, hearing device 100 may be implemented as an audio playing device, such as an earphone or headphone, configured to produce a sound to a user based on an audio signal which may be communicated by a wire or wirelessly to the hearing device. Hearing device 100 may also be implemented as a hearing instrument configured to operate as an audio playing device in an accessory functionality. Hearing device 100 may also be implemented as a hearing protection device configured to attenuate ambient sound.

Different types of hearing device 100 can also be distinguished by the position at which they are intended to be worn at the ear level of the user. Some types of hearing devices comprise a behind-the-ear part (BTE part) including a housing configured to be worn at a wearing position behind the ear of the user, which can accommodate functional components of the hearing device. Hearing devices with a BTE part can comprise, for instance, receiver-in-the-canal (RIC) hearing aids and behind-the-ear (BTE) hearing aids. Other functional components of such a hearing device may be intended to be worn at a different position at the ear, in particular at least partially inside an ear canal. For instance, a RIC hearing aid may comprise a receiver intended to be worn at least partially inside the ear canal. The receiver may be implemented in a separate housing, for instance an earpiece adapted for an insertion and/or a partial insertion into the ear canal. A BTE hearing aid may further comprise a sound conduit, for instance a sound tube, intended to be worn at least partially inside the ear canal. Other types of hearing devices, for instance earbuds, earphones, and hearing instruments such as in-the-ear (ITE) hearing aids, invisible-in-the-canal (IIC) hearing aids, and completely-in-the-canal (CIC) hearing aids, commonly comprise a housing intended to be worn at a position at the ear such that they are at least partially inserted inside the ear canal. An additional housing for wearing at the different ear position may be omitted in those devices.

In the illustrated example, hearing device 100 includes a processor 102 communicatively coupled to a sensor unit 110, a memory 103, a communication port 105, and an output transducer 107. Output transducer 107 may be implemented by any suitable audio output device, for instance a loudspeaker or a receiver of a hearing aid or an output electrode of a cochlear implant system. FIG. 1 further illustrates an exemplary remote device 120 configured to be operated remote from hearing device 100. For instance, the remote device may be a handheld device such as a smartphone or a stationary processing device such as a personal computer (PC). Remote device 120 includes a processor 122 communicatively coupled to a memory 123 and a communication port 125 configured to communicate with communication port 105 of hearing device 100. A communication system comprises hearing device 100 and remote device 120.

Sensor unit 110 comprises at least one biometric sensor 111 configured to provide biometric data. Sensor unit 110 can comprise other sensors. In the illustrated example, sensor unit 110 further comprises a sound detector 115 configured to provide sound data and a movement detector 117 configured to provide movement data. Sensor data provided by sensor unit 110 thus comprises the biometric data and can further comprise other data, in particular the sound data and/or the movement data. Each sensor 111, 115, 117 may be communicatively coupled to processor 102 via at least one dedicated signal line. Each sensor may then separately provide a respective part of the sensor data to processor 102 in an individual sensor signal or a plurality of individual sensor signals. In some instances, multiple sensors of sensor unit 110 may provide a respective part of the sensor data to processor 102 via a common signal line in a collective sensor signal.

Movement detector 117 may be implemented by any suitable sensor configured to provide movement data indicative of a movement of a user. In particular, movement detector 117 may comprise at least one inertial sensor. The inertial sensor can include, for instance, an accelerometer configured to provide the movement data representative of an acceleration and/or displacement and/or rotation, and/or a gyroscope configured to provide the movement data representative of a rotation. Movement detector 117 may also comprise an optical detector such as a camera. The movement data may be provided by generating optical detection data over time and evaluating variations of the optical detection data. Movement detector 117 may also comprise a navigation sensor such as a GPS sensor. Movement detector 117 may also comprise an electronic compass such as a magnetometer. Movement detector 117 can be configured to provide the movement data over time in subsequent periods. Movement detector 117 can be mechanically coupled to a housing of hearing device 100 such that it remains in a fixed position relative to the housing upon a translational and/or rotational displacement of the housing. Thus, the movement data provided by movement detector 117 is indicative of a movement of hearing device 100 and a corresponding movement of the user wearing hearing device 100 at an ear.

Sound detector 115 may be implemented by any suitable sound detection device, such as a microphone, in particular a microphone array, and/or a voice activity detector (VAD), and is configured to detect a sound presented to a user of hearing device 100. The sound can comprise ambient sound such as audio content (e.g., music, speech, noise, etc.) generated by one or more sound sources in an ambient environment of the user. The sound can also include audio content generated by a voice of the user during an own voice activity, such as a speech by the user. The own voice activity may be detected by a voice activity detector (VAD). The VAD may be configured to detect sound from bone conducted vibrations transmitted from the user's vocal chords to the user's ear canal and/or to estimate an own voice sound portion from sound detected by an ambient microphone and/or an ear canal microphone. In some implementations, the microphone is configured to detect body sounds such as eating, gulping, burping or digestion sounds, which may be identified by processor 102. In some implementations, sound detector 115 includes movement detector 117. In particular, the movement data provided by movement detector 117 can be indicative of an own voice activity of the user. For instance, an accelerometer may be employed as a movement detector to provide movement data indicative of a jaw movement of the user and as a VAD to detect a rhythmical vocal cord movement and thus an own voice activity of the user, as described in European patent application No. EP19166291.5. Sound detector 115 is configured to output sound data indicative of the detected sound. Sound detector 115 may be included in hearing device 100 and/or communicatively coupled to processor 102 in any suitable manner.

Memory 103 may be implemented by any suitable type of storage medium and is configured to maintain, e.g. store, data controlled by processor 102, in particular data generated, accessed, modified and/or otherwise used by processor 102. For example, processor 102 may control memory 103 to maintain a data record based on data provided by sensor unit 110. Memory 103 may also be configured to store instructions for operating hearing device 100 that can be executed by processor 102, in particular an algorithm and/or a software that can be accessed and executed by processor 102.

Communication port 105 may be implemented by any data transmitter or data transducer configured to transmit data to remote device 120. For this purpose, a communication link can be established between communication port 105 and communication port 125 of remote device 120. Communication port 105 may be configured for wireless data transmission. For instance, data may be communicated in accordance with a Bluetooth™ protocol and/or by any other type of radio frequency communication such as, for example, data communication via an internet connection and/or a mobile phone connection. The transmitted data may comprise data maintained in memory 123 of remote device 120, which may be controlled by processor 102 of hearing device 100 and/or by processor 122 of remote device 120. In particular, processor 102, 122 may be configured to control maintaining of the data record in the memory of the remote device based on sensor data provided by sensor unit 110.

Processor 102 is configured to access the sensor data provided by sensor unit 110 including the biometric data provided by biometric sensor 111. Processor 102 is also configured to determine a physiological parameter from the sensor data, to determine whether the physiological parameter fulfills a condition, and to provide, when the physiological parameter fulfills the condition, output data based on the sensor data, the output data including at least part of the biometric data and/or information derived from at least part of the biometric data. In some implementations, processor 102 is configured to initiate a transmission of the output data to remote device 120 via communication port 105. In some implementations, processor 102 is configured to store the output data in memory 103. In some implementations, processor 102 is configured to output the output data to the user via an output interface of hearing device 100. In some implementations, processor 102 is configured to control another operation of hearing device 100 based on the output data. The physiological parameter may be a first physiological parameter different from a second physiological parameter determined from the output data, for instance by processor 102 of hearing device 100 and/or by processor 122 of remote device 120. These and other operations that may be performed by processor 102, 122 are described in more detail in the description that follows.

A biometric sensor, as used herein, may be any device configured to measure a biological characteristic intrinsic to a living organism, in particular a human body. The biological characteristic may comprise any information about a physical structure, chemical process, molecular interaction, and/or physiological mechanism of the living organism. The biological characteristic may be measured by detecting any form of energy and/or matter intrinsic to the living organism and/or emitted from the living organism. For instance, the biological characteristic may be a measured blood or molecular characteristic, in particular a varying light absorption and/or reflection, and/or an amount and/or density of a molecular content in biological tissue, and/or a measured electromagnetic signal generated by the living organism and/or a measured temperature characteristic for thermal energy produced by the living organism. In some examples, the biometric sensor comprises a PPG sensor and/or an ECG sensor and/or an EEG sensor and/or an EOG sensor and/or a temperature sensor and/or a skin conductance sensor and/or an RF sensor. The biometric sensor may be configured to provide an acute measurement of the biological characteristic, for instance by directly detecting energy and/or matter from the living organism, and/or a processed collection of acute measurements of the biological characteristic, for example by recording the biological characteristic over time such as in a PPG waveform and/or a recorded EEG signal. Biometric data may be any data representative for the measured biological characteristic. The biometric sensor may provide a biometric signal containing the biometric data. Biometric information included in the biometric data may by any information about the biological characteristic.

A sensor or detector other than a biometric sensor may be any device configured to measure a characteristic which is not intrinsic to a biological function. Such a characteristic can comprise any activity of a human within an ambient environment in a vicinity of the human's body and/or a characteristic of the ambient environment. The activity may comprise any movement of the human body in the ambient environment such as a walking activity and/or head rotation and/or jaw movement and/or any other physical activity. The movement can be measured by a movement detector, e.g. an inertial sensor, configured to provide movement data. The activity may also comprise a sound, for instance a sound caused by a speech of a human. The characteristic of the ambient environment may comprise sound emitted by any sound source in the ambient environment and/or any sound produced by an output transducer of the hearing device. The sound can be measured by a sound detector, e.g. a microphone and/or a voice activity detector (VAD), configured to provide sound data. Other characteristics of the ambient environment may comprise, for instance, ambient temperature, humidity, barometric pressure, radiation, airborne particle density, and/or the like.

A physiological parameter, as used herein, may be any parameter indicative of a physiological property of the user. The physiological property can include, for instance, a heart rate, resting heart rate (RHR), heart rate variability (HRV), heart rate recovery time, heart rate variation and/or arrhythmia, blood pressure, elevated blood pressure (hypertension), saturation pressure of blood oxygen ($SpO_2$), maximum oxygen consumption ($VO_2$ max), blood glucose level, cardiovascular health, endurance level, aerobic fitness level, body temperature, sweat rate, respiratory rate, cognitive load, listening intention, listening effort, cognitive decline, breakdown of neural activity over time, sleeping or waking state, distraction level, concentration level, relaxation level, physical exhaustion level, physiological stress, and/or the like. In some instances, the physiological parameter is a parameter indicative of a quantitatively measurable physiological property such as, for instance, a rate and/or a level. In some instances, the physiological parameter is a parameter indicative of a qualitatively identifiable physiological property such as, for instance, a presence and/or absence of a physiological condition which may include, for instance, the user being in a state of his RHR and/or in a sleeping state and/or experiencing a breakdown of neural activity, or not. For instance, the physiological parameter may be provided as a binary value having a first value when such a physiological condition is met, and having a second value when such a physiological condition is not met. The condition may by any condition characteristic of a state of the physiological property, in particular a physiological condition. It may be that the physiological parameter is indicative of the physiological property such that the physiological property can be directly deduced from the physiological parameter, for instance without a further data evaluation. The physiological parameter may indicate a trend and/or a rate of change of the physiological property underlying the physiological parameter.

In some instances, the physiological parameter can be determined by an assessment of the biometric data. For instance, a heart rate and/or blood pressure and/or $VO_2$ max and/or aerobic fitness level may be determined based on biometric data provided by a PPG sensor and/or an ECG sensor. A cognitive load and/or listening effort and/or concentration level and/or physiological stress may be determined based on biometric data provided by an EEG sensor.

In some instances, the physiological parameter can be determined by an assessment of data provided by a sensor or detector other than a biometric sensor. For instance, the physiological parameter may be determined based on movement data of a movement detector which can indicate, for instance, a physical exhaustion level and/or relaxation level of the user. To illustrate, an evaluation of the movement data yielding that little or no movements have been performed by the user for a prolonged time can indicate a small physical exhaustion level of the user and/or a high relaxation level of the user. As another example, the physiological parameter may be determined based on sound data of a sound detector which may also serve as a physiological indicator, e.g. for a relaxation level and/or a distraction level of the user. To illustrate, an evaluation of the sound data revealing silence to a certain degree for a while in the ambient environment of the user can indicate a high relaxation level and/or a small distraction level of the user.

Figure 2:
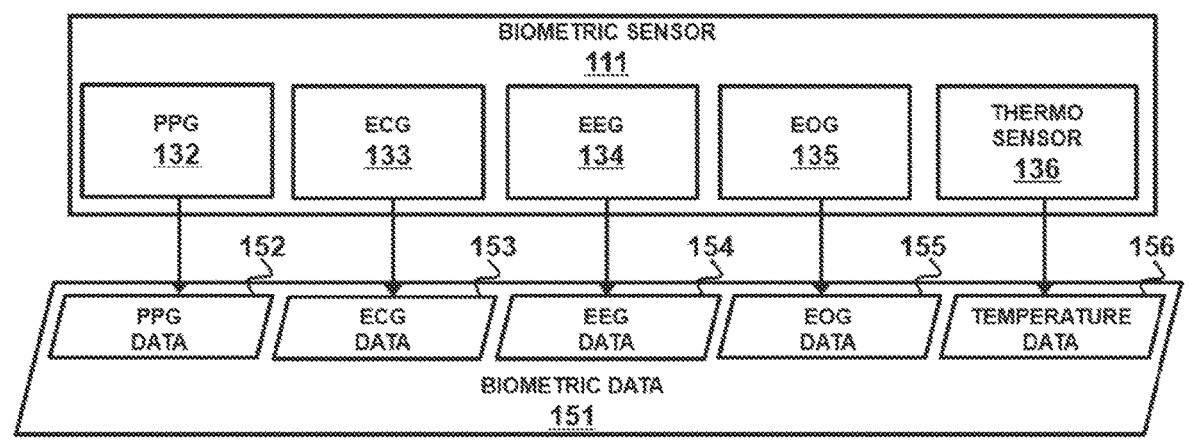
FIG. 2 schematically illustrates exemplary embodiments of biometric sensors that can be implemented in the hearing device illustrated in FIG. 1.

FIG. 2 illustrates exemplary implementations of biometric sensor 111, and biometric data 151 provided by biometric sensor 111. Biometric sensor 111 comprises a PPG sensor 132 configured to provide PPG data 152 and/or an ECG sensor 133 configured to provide ECG data 153 and/or an EEG sensor 134 configured to provide EEG data 154 and/or an EOG sensor 135 configured to provide EOG data 155 and/or a temperature sensor 136 configured to provide temperature data 156 and/or a skin conductance sensor providing skin conductance data and/or an RF sensor providing reflection or absorption data to specific frequencies. In the place of biometric sensor 111 illustrated in FIG. 1, any of sensors 132-136 can be provided or any combination thereof. Biometric data 151 can comprise at least one of data 152-156 or any combination thereof. In some instances, multiple sensors 132-136 are communicatively coupled to processor 102 via a separate signal line such that the respective data 152-156 can be supplied to processor 102 in individual sensor signals. In some instances, multiple sensors 132-136 are communicatively coupled to processor 102 via a common signal line such that the respective data 152-156 can be supplied to processor 102 in a collective sensor signal.

Biometric sensor 111 can comprise at least one optical sensor. The optical sensor can comprise at least one light source configured to emit light and at least one optical detector for detecting a reflected and/or scattered part of the light. The light source, for instance a light emitting diode (LED), can be directed to a skin of the user. A wavelength of the light source may be selected such that at least part of the emitted light penetrates a skin of the user and can be absorbed by blood flowing through the user underneath a surface of the skin. PPG sensor 132 may comprise at least one optical sensor.

Biometric sensor 111 can comprise at least one electrode. The electrode can be configured to detect an electric signal induced through a skin of the user. In particular, the electrode can be configured to pick up a low voltage electric signal from the skin and/or to determine an electric potential present between the skin and the environment and/or between different portions of the skin. The electrode may be configured to be placed at a skin of the user such that the electrode is in contact with the skin. ECG sensor 133 and/or EEG sensor 134 and/or EOG sensor 135 may comprise at least one electrode, in some instances at least two electrodes having a distance which may be bridged by the user's skin.

Temperature sensor 136 may be sensitive to thermal radiation and/or conduction and/or convection and/or heat flow. For instance, temperature sensor 136 may include a thermistor, thermopile, thermocouple, solid state sensor, and/or the like. Temperature sensor 136 may comprise a plurality of thermosensitive components. Temperature sensor 136 may thus be configured to measure temperature at multiple regions of the ear, for instance at the inner ear and the outer ear, in order to provide information about the heat flowing between those regions.

A physiological parameter may be determined from any data 152-156 included in biometric data 151. In some instances, the physiological parameter is determined from data 152-156 separately provided by any of sensors 132-136. For instance, a heart rate and/or blood pressure may be determined from PPG data 152 or ECG data 153. A cognitive load may be determined from EEG data 153. A body temperature may be determined from temperature data 156. In some instances, the physiological parameter is determined from data 152-156 provided by a combination of sensors 132-136. For instance, a heart rate and/or blood pressure may be determined from PPG data 152 and ECG data 153. A cognitive load associated with a certain body temperature may be determined from EEG data 153 and temperature data 156. Combining information of data provided by multiple sensors 132-136 can be used, for instance, to increase a reliability of the determined physiological parameter and/or to evaluate a mutual dependency of different physiological parameters.

Figure 3:
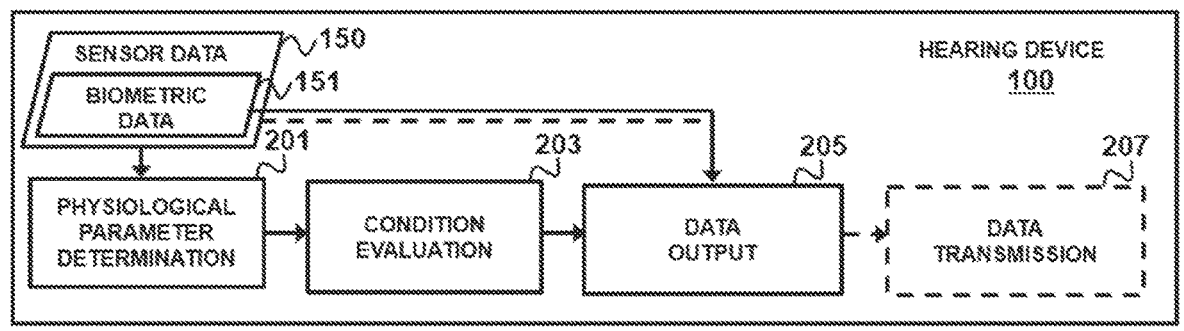
FIGS. 3 and 4 schematically illustrate exemplary configurations of a hearing device to determine from sensor data a physiological parameter and to provide output data depending on the physiological parameter fulfilling a condition.

FIG. 3 illustrates a functional block diagram of an exemplary sensor data processing algorithm that may be executed by processor 102. As shown, the algorithm is configured to be applied to sensor data 150 comprising biometric data 151 provided by biometric sensor 111. The sensor data is input to processor 102. The algorithm comprises modules 201-207.

A physiological parameter determination module 201 can determine a physiological parameter indicative of a physiological property of the user from sensor data 150. The physiological parameter can be determined from biometric data 151 and/or from data provided by a sensor or detector other than biometric sensor 111, for instance sound detector 115 and/or movement detector 117. Physiological parameter determination module 201 can be configured to monitor sensor data 150 over a period to determine the physiological parameter over the period.

A condition evaluation module 203 can determine whether the physiological parameter fulfills a condition, in particular whether the physiological parameter determined over the period fulfills the condition. In some implementations, the condition is representative for a state of the physiological property. Condition evaluation module 203 can thus be employed to determine whether the user is in the state of the physiological property, or not.

A data output module 205 can provide output data based on the sensor data. The output data is provided depending on whether the physiological parameter has been determined to fulfill the condition by condition evaluation module 203. The output data includes at least part of biometric data 151 and/or information derived from at least part of biometric data 151, as indicated by a solid arrow leading to data output module 205 in FIG. 3. The output data can further include at least a part of sensor data 150 other than biometric data 151 and/or information derived from at least a part of sensor data 150 other than biometric data 151, as indicated by a dashed arrow leading to data output module 205 in FIG. 3. In some implementations, the output data can be output via an output interface, for instance a display and/or an audio message, and/or stored in memory 103 and/or employed to control another operation of hearing device 100, for instance adjusting a sound level of sound output by output transducer 107 and/or adjusting a directivity of acoustic beamforming performed by processor 102.

In some implementations, the output data can be transmitted to remote device 120 via communication port 105. A data transmission module 207 can initiate the transmission of the output data. In some instances, data transmission module 207 is configured to transmit the output data to remote device 120 immediately after the physiological parameter has been determined to fulfill the condition by condition evaluation module 203. In some instances, data transmission module 207 is configured to transmit the output data to remote device 120 after the physiological parameter has been determined to fulfill the condition by condition evaluation module 203 and after determining that a data connection has been established with remote device 120. In some instances, data transmission module 207 is configured to transmit the output data to remote device 120 at a predetermined schedule, for instance for a predetermined number of times per day and/or at a predetermined time each day. In some instances, the output data is stored in memory 103 and accessed by data transmission module 207 before the data transmission, for instance in cases in which the output data is transmitted not immediately after the physiological parameter has been determined to fulfill the condition by condition evaluation module 203.

Figure 4:
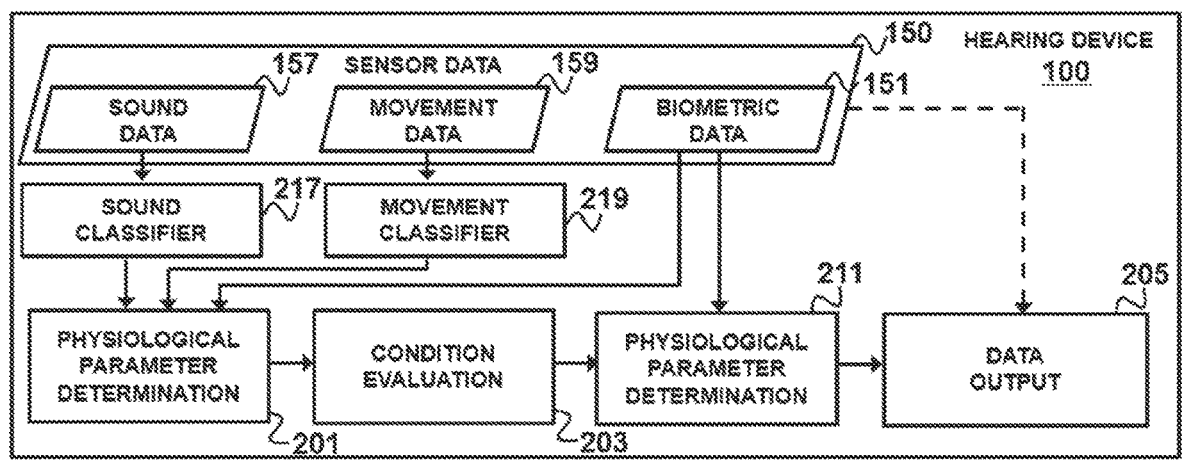

FIG. 4 illustrates a functional block diagram of an exemplary sensor data processing algorithm that may be executed by processor 102. As shown, the algorithm is configured to be applied to sensor data 150 comprising biometric data 151 provided by biometric sensor 111, sound data 157 provided by sound detector 115, and movement data 159 provided by movement detector 117. The sensor data is input to processor 102. The algorithm comprises modules 211, 217, 219 in addition to modules 201, 203, 205 described above.

Sound data 157 is input to a sound classifier module 217. Sound classifier 217 is configured to assign sound data 157 to a class from a number of predefined classes. Each class may correspond to a different category of the detected sound. Sound classifier 217 can be configured to be set in a predefined state depending on the category assigned to sound data 157. A signal processing of sound data 157 performed by processor 102 can depend on the state of sound classifier. Different states of sound classifier 217 and/or different classes of sound data 157 can depend on features extracted from sound data 157. The features may include, for instance, amplitudes, amplitude onsets, frequency contents, amplitude modulations, frequency modulations, spectral profiles, rhythm, content based indexing and/or the like. Different states of sound classifier 217 can include, for instance, a quiet state representing a quiet scene in the ambient environment, a clean speech state representing a speech at a low signal to noise ratio (SNR), a speech in noise state representing a speech at a high SNR, a noise state representing a high SNR, a music state representing the user listening to music content, and/or the like.

Movement data 159 is input to a movement classifier module 219. Movement classifier 219 is configured to assign movement data 159 to a class from a number of predefined classes. Each class may correspond to a different category of the detected movement of the user. The classes may allow to differentiate between, for instance, an activity status of the user and/or a posture status of the user and/or a wearing status of hearing device 100. Different classes of the activity status may comprise, for instance, a physical activity carried out by the user above an activity threshold, and a physical activity carried out by the user below an activity threshold, for example substantially no physical activity carried out by the user at least in a statistical sense, for instance in average or to a certain percentile. Different classes of the posture status may comprise, for instance, the user determined in an upright body position, for instance in a standing and/or walking position, and the user determined in a reclined body position, for instance in a sitting and/or lying position. Different classes of the wearing status may comprise, for instance, the hearing device determined to be at a position on the users body, for example to be worn at the user's ear, and the hearing device determined to be at a position off the users body, for example being placed inside a charging station.

The class of sound data 157 determined by sound classifier module 217 and the class of movement data 159 determined by movement classifier module 219 is input to physiological parameter determination module 201 to determine a physiological parameter from sensor data 150. Physiological parameter determination module 201 can be configured to monitor the classes over a period to determine the physiological parameter over the period. In some implementations, the monitored classes comprise at least one class determined from sound data 157, and at least one class determined from movement data 159. To illustrate, the monitored classes may comprise the class of sound classifier 217 in the quiet state and the class of the activity status below the activity threshold and/or the class of the posture status in the reclined body position and/or the class of the wearing status at the wearing position on the user's body. For instance, the period over which the classes are monitored can correspond to at least 5 minutes. For instance, the physiological parameter determined in such a way may be indicative of a relaxation level of the user. In particular, a situation may be determined in which the user is in a silent environment and is not engaged in a physical activity for a while allowing to conclude that the user is in a relaxed state.

Biometric data 151 may also be input to a classifier module configured to assign biometric data 151 to a class from a number of predefined classes, which is not shown in FIG. 4, before biometric information included in biometric data 151 is input to physiological parameter determination module 201 to determine a physiological parameter from sensor data 150. For instance, EEG data 153 may be input in physiological parameter determination module 201 to determine a concentration level of the user which may give further evidence for the relaxation level of the user. In some instances, only sound information included in sound data 157 is input to physiological parameter determination module 201. In some instances, only movement information included in movement data 159 is input to physiological parameter determination module 201. In some instances, only biometric information included in biometric data 151 is input to physiological parameter determination module 201. In some instances, information included in at least two of sound data 157, movement data 159, and biometric data 151 is input to physiological parameter determination module 201. In some instances, combined information included in sound data 157, movement data 159, and biometric data 151 is input to physiological parameter determination module 201. Providing the information from combined data 151, 157, 159 can increase the reliability of determining the physiological parameter from sensor data 150.

Condition evaluation module 203 then determines whether the physiological parameter fulfills a condition. To this effect, condition evaluation module 203 can determine whether at least one of the classes determined from sound data 157 and/or from movement data 159 and/or from biometric data 151 has been present within the period for a minimum number of times within the period. For instance, the period over which the classes are determined to be present can correspond to the period at which the classes are monitored by physiological parameter determination module 201. When at least one class determined from sound data 157 and/or at least one class determined from movement data 159 and/or at least one class determined from biometric data 151 has been determined to be present for a minimum number of times within the period, the condition may be determined to be fulfilled by the physiological parameter.

For instance, a high relaxation level of the user may be thus determined. In some instances, the high relaxation level of the user is determined when at least two of the above mentioned classes determined from sound data 157 and from movement data 159 and from biometric data 151 have been determined to be present within the period for the minimum number of times. In some instances, the high relaxation level of the user is determined when all classes have been determined to be present within the period for the minimum number of times.

Physiological parameter determination module 201 is a first physiological parameter determination module. When the physiological parameter is determined to fulfill the condition by condition evaluation module 203, a second physiological parameter determination module 211 is employed. Biometric data 151 is input to second physiological parameter determination module 211. Physiological parameter determination module 211 is configured to determine a physiological parameter from biometric data 151 which depends on another physiological parameter fulfilling the condition, as determined by condition evaluation module 203. To illustrate, when the user is determined to be at a high relaxation level by condition evaluation module 203, physiological parameter determination module 211 can determine a physiological parameter from biometric data 151 depending on the user having a high relaxation level. A physiological parameter determined by first physiological parameter determination module 201 may be denoted as a first physiological parameter, and a physiological parameter determined by second physiological parameter determination module 201 may be denoted as a second physiological parameter.

In some implementations, a resting heart rare (RHR) is determined by physiological parameter determination module 211 from biometric data 151. To this end, a heart rate may be determined from biometric data 151 which may be attributed to the user's RHR due to the condition of the user having a high relaxation level determined by condition evaluation module 203. Biometric data 151 may comprise PPG data 152 and/or ECG data 153 from which the heart rate can be determined. In some implementations, a body temperature characteristic for the user at a high relaxation level may be determined from biometric data 151. Biometric data 151 may comprise temperature data 156 from which the body temperature can be determined. In some implementations, a neural activity characteristic for the user at a high relaxation level may be determined from biometric data 151. Biometric data 151 may comprise EEG data 154 from which the neural activity can be determined.

The physiological parameter determined from biometric data 151 depending on another physiological parameter fulfilling the condition may be employed in subsequent determinations of a physiological parameter from biometric data 151 as a condition to be fulfilled. In particular, the RHR and/or the body temperature and/or the neural activity characteristic for the user at a high relaxation level may be employed as a benchmark for the heart rate and/or body temperature and/or neural activity to be fulfilled as a condition. The condition to be fulfilled may be determined by condition evaluation module 203 based on a physiological parameter determined by physiological parameter determination module 201 from biometric data 151.

Data output module 205 then provides output data based on the information derived by second physiological parameter determination module 211 from biometric data 151 depending on the physiological parameter determined by first physiological parameter determination module 201 fulfilling the condition. The output data may include other data from sensor data 150 and/or other information derived from sensor data 150, as indicated by a dashed arrow in FIG. 4. In some implementations, data transmission module 207 is employed to transmit the output data to remote device 120.

Figure 5:
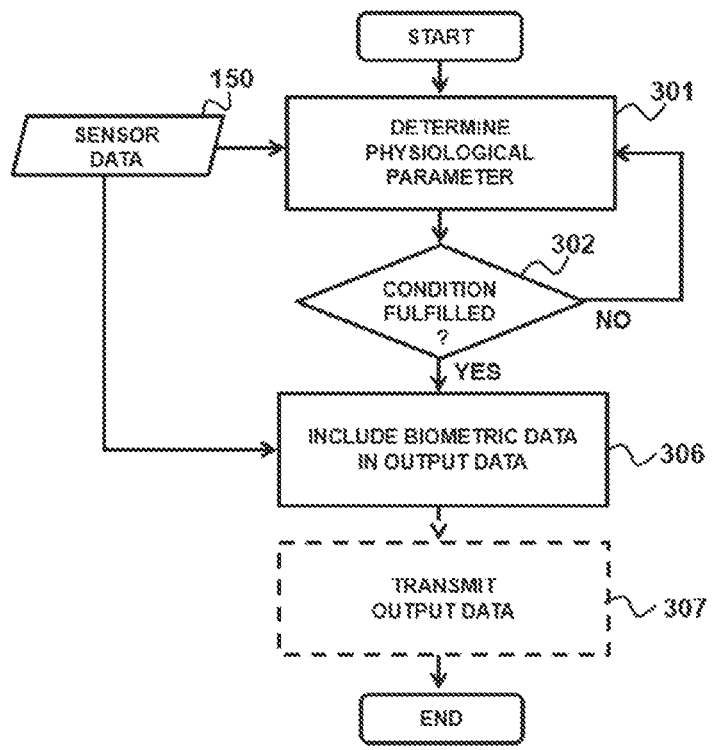
FIGS. 5-10 illustrate exemplary methods of operating a hearing device and/or a remote device according to principles described herein.

FIG. 5 illustrates a block flow diagram for a method of operating a hearing device. The method may be executed by processor 102, in particular by executing the data processing algorithm illustrated in FIG. 3 or 4. At 301, a physiological parameter indicative of a physiological property of the user is determined from sensor data 150. At 302, it is determined whether the physiological parameter fulfills a condition. In a case in which the physiological parameter does not fulfill the condition, determining the physiological parameter from sensor data 150 is repeated at 301. In a case in which the physiological parameter does fulfill the condition, output data is provided based on sensor data 150 at 306 by including biometric data 151 included in sensor data 150 in the output data. In this way, a dependency of the biometric data 151 included in the output data from the physiological parameter determined at 301 can be resolved. The included biometric data 151 may be data provided by biometric sensor 111 substantially unprocessed by processor 102. Subsequently, at 307, the output data may be transmitted to remote device 120.

In some instances, the physiological parameter is repeatedly determined over a period at 301. Correspondingly, sensor data 150 may be repeatedly provided over the period. Determining whether the physiological parameter fulfills the condition at 302 may be repeatedly performed at a predetermined rate within the period, for instance each time at which the physiological parameter is determined at 301 and/or in a statistical evaluation, for instance as a running average and/or a certain running percentile. The output data may be provided at 306 when the physiological parameter fulfills the condition within the period at a predetermined number of times, for instance each time, at which the physiological parameter is determined at 301.

Determining whether the condition is fulfilled at 302 may comprise evaluating the physiological parameter relative to a threshold. In some implementations, the threshold is a predefined value of the physiological parameter. To illustrate, the threshold may be a predetermined value of the heart rate and/or blood pressure and/or body temperature and/or cognitive load and/or relaxation level of the user. In some instances, the condition is determined to be fulfilled when the physiological parameter falls below the threshold. In some instances, the condition is determined to be fulfilled when the physiological parameter rises above the threshold.

Figure 6:
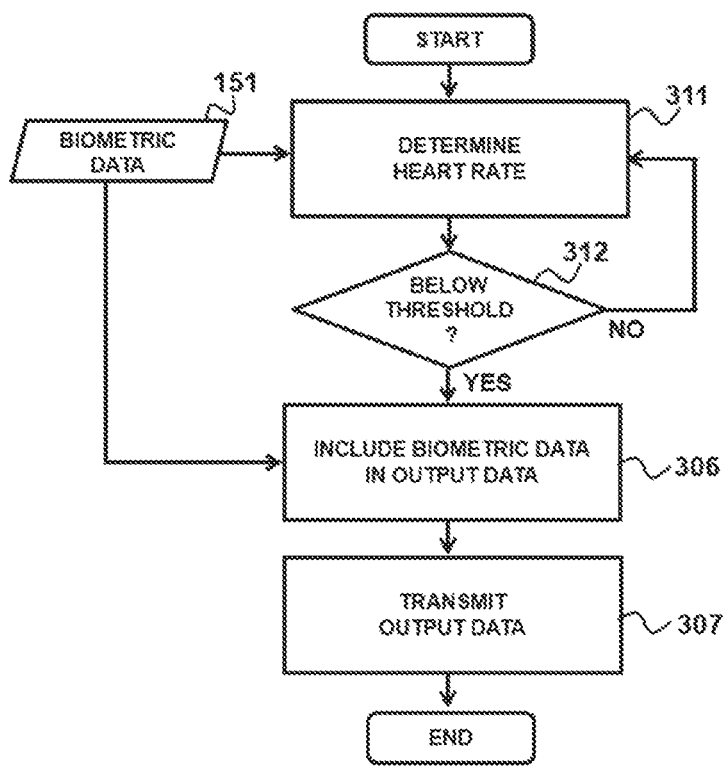

FIG. 6 illustrates a block flow diagram for a method of operating a hearing device. The method represents some implementations of the method illustrated in FIG. 5. At 311, a heart rate of the user is determined from biometric data 150 as the physiological parameter. At 312, it is determined whether the heart rate is below a threshold. When the heart rate is found to be above the threshold, the physiological parameter is determined to not fulfill the condition, and determining the heart rate from biometric data 150 is repeated at 311. When the heart rate is found to be below the threshold, the physiological parameter is determined to fulfill the condition and at least part of biometric data 151 is included in the output data at 306. At 307, the output data is transmitted to remote device.

In some implementations, the threshold is selected such that the heart rate determined at 311 substantially corresponds to the RHR of the user when the heart rate is found to be below the threshold at 312. Determining whether the condition is fulfilled at 302 thus may be implemented by determining whether the heart rate corresponds to the RHR at 312. Determining whether the heart rate corresponds to the RHR may also be implemented in different ways than comparing the heart rate determined at 311 to the threshold at 312. For instance, the heart rate determined at 311 may be evaluated with respect to a distinct value or value range corresponding to the RHR. Determining whether the heart rate corresponds to the RHR may also be implemented by steps 351-355 of the method illustrated in FIG. 10, as further described below. Determining the heart rate at 311 and determining whether the heart rate corresponds to the RHR at 312 may be repeatedly performed over a period. In this way, it can be ensured that the user is in a physiological state of his RHR for a minimum amount of time. For instance, the period may be selected to be at least 5 minutes.

Figure 7:
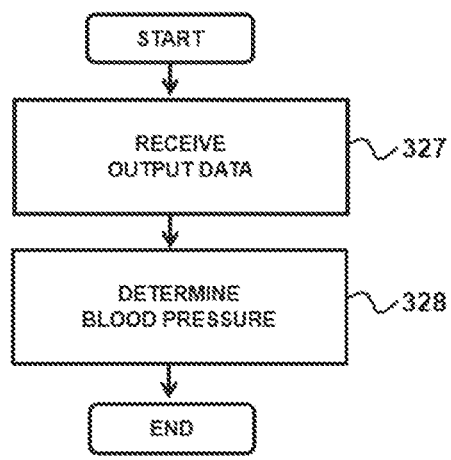

FIG. 7 illustrates a block flow diagram for a method of operating a remote device to which output data is transmitted from a hearing device at 307 in the method illustrated in FIG. 5 or FIG. 6. The method may be executed by processor 122 of remote device 120. The physiological parameter determined at 301 and/or at 311 is a first physiological parameter indicative of a first physiological property. At 327, the output data comprising at least part of biometric data 151 is received. At 328, a second physiological parameter indicative of second physiological property is determined from biometric data 151 included in the output data. In the illustrated example, the second physiological parameter is a blood pressure of the user indicative for a blood pressure at the RHR of the user. For instance, biometric data 151 may comprise PPG data 132 and/or ECG data 153 based on which the blood pressure may be determined. In addition, movement data 159 may be included in output data at 306, which may be employed by remote device to determine the blood pressure. In this way, a larger processing power and/or a longer battery life of remote device 120 can be advantageously exploited to determine the physiological parameter at 328.

In some instances, biometric data 132 included in the output data at 307 is raw data as provided by biometric sensor 111 unprocessed by processor 102 of hearing device 102. For instance, biometric data 132 included in the output data at 307 may comprise PPG data 132 as provided by PPG sensor 132 and/or ECG data 153 as provided by ECG sensor 133, wherein processor 102 does not perform any further processing of the data. Remote device 120 can thus be enabled to determine the physiological parameter from biometric data 132 as originally provided by biometric sensor 111. In some instances, biometric data 132 included in the output data at 307 is pre-processed by processor 102 of hearing device 102, for instance to remove noise and/or movement artifacts, wherein biometric data 132 included in the output data at 307 contains the same amount of biometric information as the raw data provided by biometric sensor 111.

Moreover, providing the output data at 306 by the hearing device and transmitting the output data at 307 to the remote device depending on the condition to be fulfilled, for instance the heart rate determined to be below the threshold at 312 and/or a relaxation level of the user being above a threshold, can ensure that that the output data is only transmitted when biometric data 151 is representative of a certain physiological condition, for instance that the user is in a physiological state of his RHR. In this way, the physiological parameter, for instance the blood pressure, determined by remote device at 328 can also be representative for the physiological condition being met. The data transmission from the hearing device to the remote device can thus be advantageously reduced to a number of times in which determining the physiological parameter by the remote device at 328 is relevant for the determining of the physiological parameter, for instance at a condition in which determining the physiological parameter can be meaningful in a medical sense. To illustrate, a meaningful measurement of the blood pressure can imply the user being in a state of his RHR. Therefore, only biometric data 151 relevant for determining the blood pressure may be transmitted from hearing device 100 to remote device 120, which is biometric data 151 for which the condition of the user being in the state of his RHR is fulfilled. This can allow to further reduce the energy consumption of the hearing device required for determining the physiological parameter in a useful way.

Figure 8:
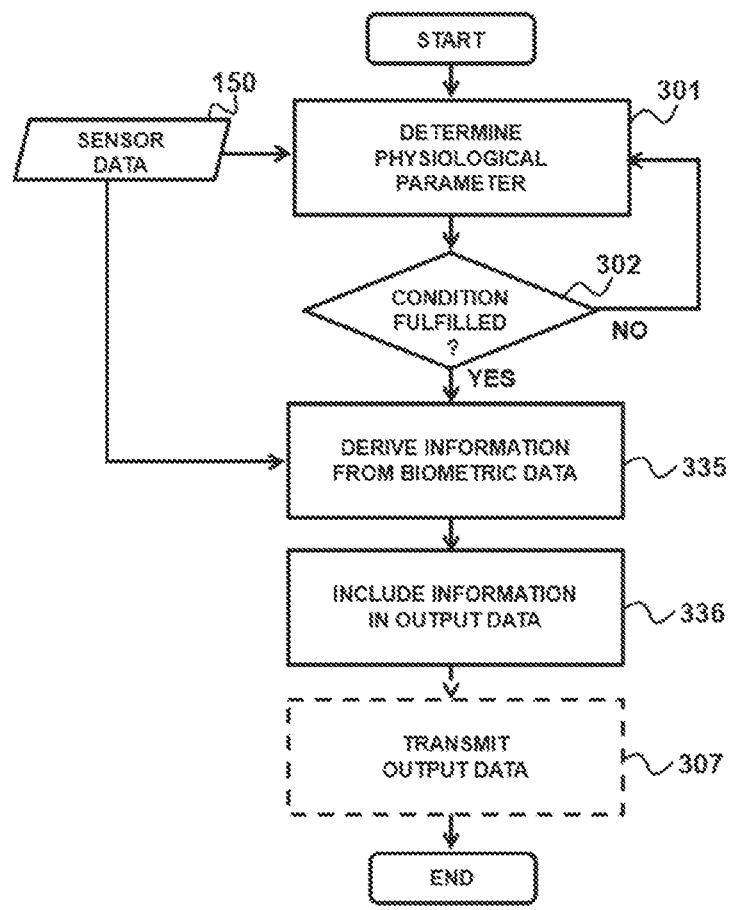

FIG. 8 illustrates a block flow diagram for a method of operating a hearing device. The method may be executed by processor 102, in particular by executing the data processing algorithm illustrated in FIG. 3 or 4. After determining at 302 whether the physiological parameter determined from sensor data 150 at 301 fulfills the condition, information is derived at 335 from biometric data 151 included in sensor data 150 when the physiological parameter fulfills the condition. At 336, output data is provided by including the information derived at 335 in the output data. In some instances, biometric data 151 and/or other data included in sensor data 150 may be included in the output data. Subsequently, at 307, the output data may be transmitted to remote device 120.

Deriving the information at 335 can comprise determining a physiological parameter from biometric data 151 included in sensor data 150. The physiological parameter determined at 335 can be different from the physiological parameter determined at 301. For example, a first physiological parameter determined at 301 may be related to a neural activity of the user and a second physiological parameter determined at 335 may be related to a body temperature of the user. As another example, a first physiological parameter determined at 301 may be related to a first blood parameter of the user and the second physiological parameter determined at 335 may be related to a second blood parameter of the user. In this way, a dependency of the physiological parameter determined at 335 from the physiological parameter determined at 301 can be resolved. The first physiological parameter determined at 301 may be indicative for the same physiological property as the first physiological parameter determined at 335. The first physiological parameter determined at 301 may also be indicative for a different physiological property than the first physiological parameter determined at 335.

Figure 9:
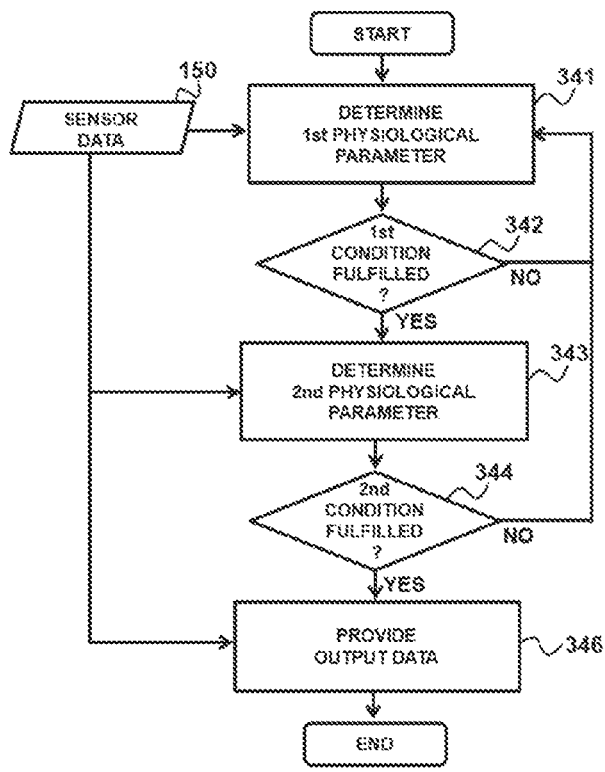

FIG. 9 illustrates a block flow diagram for a method of operating a hearing device. The method may be executed by processor 102, in particular by executing the data processing algorithm illustrated in FIG. 3 or 4. At 341, a first physiological parameter indicative of a physiological property of the user is determined from sensor data 150. At 342, it is determined whether the first physiological parameter fulfills a first condition. In a case in which the first physiological parameter does not fulfill the first condition, determining the first physiological parameter from sensor data 150 is repeated at 341. Steps 341 and 342 may be carried out corresponding to steps 301 and 302 of the method illustrated in FIG. 5 and in FIG. 8. In a case in which the first physiological parameter does fulfill the first condition, a second physiological parameter indicative of a physiological property of the user is determined at 343 from sensor data 150. At 344, it is determined whether the second physiological parameter fulfills a second condition. In a case in which the second physiological parameter does not fulfill the second condition, determining the first physiological parameter from sensor data 150 is repeated at 341. Steps 343 and 344 may also be carried out corresponding to steps 301 and 302 of the method illustrated in FIG. 5 and in FIG. 8. In a case in which the second physiological parameter does fulfill the second condition, output data is provided at 346. Providing the output data at 346 may comprise step 306 of the method illustrated in FIG. 5 and/or steps 335 and 336 of the method illustrated in FIG. 8. In some instances, providing the output data at 346 further comprises step 307 of transmitting the output data from hearing device 100 to remote device 120.

The output data provided at 346 thus includes at least part of biometric data 151 included in sensor data 150 and/or information derived from at least part of biometric data 151 included in sensor data 150 different from the first physiological parameter and the second physiological parameter. In this way, a dependency of biometric data 151 included in the output data and/or of the information derived from biometric data 151 included in sensor data 150 from the first physiological parameter determined at 341 and the second physiological parameter determined at 343 can be resolved. For example, the first physiological parameter determined at 341 may be related to a physical exhaustion level of the user and the second physiological parameter determined at 343 may be related to a concentration level of the user. The output data provided at 346 can thus depend on the physical exhaustion level and the concentration level of the user. Information derived from at least part of biometric data 151 included in the output data may comprise a third physiological parameter different from the first physiological parameter and the second physiological parameter. The third physiological parameter may be indicative for the same physiological property as at least one of the first physiological parameter and the second physiological parameter or for a different physiological property as the first physiological parameter and the second physiological parameter.

Figure 10:
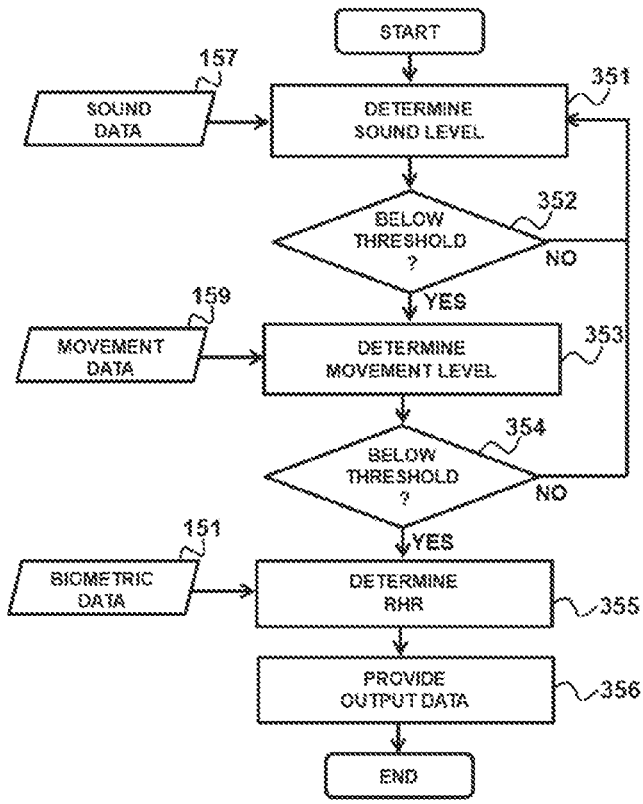

FIG. 10 illustrates a block flow diagram for a method of operating a hearing device. The method represents some implementations of the method illustrated in FIG. 9. At 351, a sound level is determined from sound data 157 included in sensor data 150. Determining the sound level may be performed by sound classifier 217. The sound level can be a first indicator of a relaxation level of the user corresponding to a first physiological parameter determined at 341. At 352, it is determined whether the first physiological parameter fulfills the first condition that the sound level is below a threshold indicating a high relaxation level of the user. When the sound level is found to be above the threshold, the first physiological parameter is determined to not fulfill the condition, and determining the sound level from sound data 157 is repeated at 351.

When the sound level is found to be below the threshold, a movement level is determined at 353 from movement data 159 included in sensor data 150. Determining the movement level may be performed by movement classifier 219. The movement level can be a second indicator of a relaxation level of the user corresponding to a second physiological parameter determined at 343. The sound level determined as the first physiological parameter from sound data 157 and the movement level determined as the second physiological parameter from movement data 159 are thus indicative for the same physiological property of the relaxation level of the user. At 354, it is determined whether the second physiological parameter fulfills the second condition that the movement level is below a threshold providing further evidence of a high relaxation level of the user. When the movement level is found to be above the threshold, the second physiological parameter is determined to not fulfill the condition, and determining the sound level from sound data 157 is repeated at 351.

When the movement level is found to be below the threshold, a heart rate is determined at 355 from biometric data 151 included in sensor data 150, for instance from PPG data 152 and/or ECG data 153. Since the heart rate determined at 355 depends on the user being in a physiological state of a high relaxation level, as determined at 352 and 354, the heart rate determined at 355 is the heart of the user at the high relaxation level. The determined heart rate can thus be attributed to the RHR of the user. Subsequently, output data is provided at 356. Providing the output data at 356 may comprise step 306 of the method illustrated in FIG. 5 and/or steps 335 and 336 of the method illustrated in FIG. 8. In some instances, providing the output data at 356 further comprises step 307 of transmitting the output data from hearing device 100 to remote device 120. After receiving the output data, remote device 120 may determine a physiological parameter from the output data different from the physiological parameters determined by the hearing device. In particular, the method illustrated in FIG. 7 may be performed by remote device 120.

In some implementations, steps 351-355 may be performed in the method illustrated in FIG. 6 in the place of steps 311, 312. When the heart rate is attributed to the RHR of the user at 355, the condition of the heart rate corresponding to the RHR is equally determined to be fulfilled. Subsequently, at least part of biometric data 151 is included in the output data at 306, and the output data is transmitted to remote device 120 at 307. Remote device 120 may then perform the method illustrated in FIG. 7 to determine a third physiological parameter from biometric data 151 included in the output data, for instance a blood pressure of the user. The thus determined physiological parameter determined by remote device 120 is equally representative of a condition in which the user is in a state of his RHR. For instance, the blood pressure may thus be determined under a condition in which the determined parameter value is meaningful in a medical sense requiring the user being in a state of his RHR.

While the principles of the disclosure have been described above in connection with specific devices and methods, it is to be clearly understood that this description is made only by way of example and not as limitation on the scope of the invention. The above described preferred embodiments are intended to illustrate the principles of the invention, but not to limit the scope of the invention. Various other embodiments and modifications to those preferred embodiments may be made by those skilled in the art without departing from the scope of the present invention that is solely defined by the claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

What is claimed is:

1. A hearing device configured to be worn at an ear of a user, the hearing device comprising:
   a sensor unit configured to provide sensor data, the sensor unit comprising a sound detector configured to provide sound data included in the sensor data; and
   a processor configured to determine a physiological parameter at least partially from the sound data included in the sensor data, the physiological parameter indicative of a physiological property of the user;
   wherein the processor is further configured to
      determine whether the physiological parameter fulfills a condition; and
      provide, depending on whether the physiological parameter fulfills the condition, output data based on the sensor data,
   wherein:
      the physiological parameter is indicative of a heart rate of the user; and
      the determining whether the condition is fulfilled comprises determining, based on the sound data, whether the heart rate corresponds to a resting heart rate of the user.

2. The hearing device of claim 1, wherein:
   the sensor unit further comprises a biometric sensor configured to provide biometric data included in the sensor data;
   the output data includes at least part of at least one of the biometric data or information derived from at least part of the biometric data different from the physiological parameter; and
   biometric information in the biometric data included in the output data is unmodified by the processor.

3. The hearing device of claim 1, wherein:
   the physiological parameter is indicative of a relaxation level of the user; and the determining whether the condition is fulfilled comprises determining whether the physiological parameter is above a threshold.

4. The hearing device of claim 1, wherein:
the sensor unit further comprises a biometric sensor configured to provide biometric data included in the sensor data; and
the physiological parameter is at least partially determined from the biometric data.

5. The hearing device of claim 1, wherein:
the sensor unit further comprises a movement detector configured to provide movement data included in the sensor data; and
the physiological parameter is at least partially determined from the movement data.

6. The hearing device of claim 1, wherein the determining of whether the physiological parameter fulfills the condition includes determining whether the physiological parameter fulfills the condition a predetermined number of times during a period of time.

7. The hearing device of claim 1, wherein:
the sensor unit further comprises a biometric sensor configured to provide biometric data included in the sensor data;
the biometric sensor comprises a light source configured to emit light through a skin of the user and an optical detector for detecting at least one of a reflected part or a scattered part of the light; and
the biometric data comprises information about the detected light.

8. The hearing device of claim 1, wherein:
the sensor unit further comprises a biometric sensor configured to provide biometric data included in the sensor data;
the biometric sensor comprises an electrode configured to detect an electric signal induced through a skin of the user; and
the biometric data comprises information about the electric signal.

9. The hearing device of claim 1, wherein:
the sensor unit further comprises a biometric sensor configured to provide biometric data included in the sensor data;
the biometric sensor comprises a temperature sensor configured to detect a body temperature of the user; and
the biometric data comprises information about the body temperature.

10. The hearing device of claim 1, wherein:
the hearing device further comprises a communication port configured to transmit data to a remote device; and
the processor is configured to provide the output data to the communication port.

11. A communication system comprising:
a hearing device configured to be worn at an ear of a user, the hearing device comprising:
a sensor unit configured to provide sensor data, the sensor unit comprising a sound detector configured to provide sound data included in the sensor data;
a processor configured to determine a physiological parameter at least partially from the sound data included in the sensor data, the physiological parameter indicative of a physiological property of the user;
wherein the processor is further configured to
determine whether the physiological parameter fulfills a condition; and
provide, depending on whether the physiological parameter fulfills the condition, output data based on the sensor data; and
a remote device comprising a communication port configured to receive the output data from the hearing device,
wherein:
the physiological parameter is indicative of a heart rate of the user; and
the determining whether the condition is fulfilled comprises determining, based on the sound data, whether the heart rate corresponds to a resting heart rate of the user.

12. The communication system of claim 11, wherein the remote device comprises a processor, the processor configured to determine a physiological parameter from the output data, the physiological parameter determined by the processor of the remote device different from the physiological parameter determined by the processor of the hearing device.

13. A method of operating a hearing device configured to be worn at an ear of a user, the method comprising:
providing sensor data including sound data detected by a sound detector; and
determining a physiological parameter at least partially from the sound data included in the sensor data, the physiological parameter indicative of a physiological property of the user;
the determining the physiological parameter including:
determining whether the physiological parameter fulfills a condition; and
providing, depending on whether the physiological parameter fulfills the condition, output data based on the sensor data,
wherein:
the physiological parameter is indicative of a heart rate of the user; and
the determining whether the condition is fulfilled comprises determining, based on the sound data, whether the heart rate corresponds to a resting heart rate of the user.

14. The method of claim 13, wherein:
the sensor data further includes biometric data detected from the user;
the output data includes at least part of at least one of the biometric data or information derived from at least part of the biometric data different from the physiological parameter; and
biometric information in the biometric data included in the output data is unmodified.

15. The method of claim 13, wherein:
the physiological parameter is indicative of a relaxation level of the user; and
the determining whether the condition is fulfilled comprises determining whether the physiological parameter is above a threshold.

16. The method of claim 13, wherein:
the sensor data includes biometric data detected from the user; and
the physiological parameter is at least partially determined from the biometric data.

17. The method of claim 13, wherein the physiological parameter is at least partially determined from movement data provided by a movement detector of the hearing device.

18. The method of claim 13, wherein the determining of whether the physiological parameter fulfills the condition includes determining whether the physiological parameter fulfills the condition a predetermined number of times during a period of time.

* * * * *